US012571015B2

(12) United States Patent
Terfehr et al.

(10) Patent No.: US 12,571,015 B2
(45) Date of Patent: Mar. 10, 2026

(54) PROCESS FOR PRODUCING ALTERNAN-OLIGOSACCHARIDE

(71) Applicant: SOCIÉTÉ DES PRODUITS NESTLÉ S.A., Vevey (CH)

(72) Inventors: Dominik Terfehr, Velbert (DE); Ralf Feldmann, Neuss (DE); Michael Puls, Monheim am Rhein (DE)

(73) Assignee: Societe des Produits Nestle S.A., Vevey (CH)

( * ) Notice: Subject to any disclaimer, the term of this patent is extended or adjusted under 35 U.S.C. 154(b) by 717 days.

(21) Appl. No.: 17/791,400

(22) PCT Filed: Jan. 8, 2021

(86) PCT No.: PCT/EP2021/050287
§ 371 (c)(1),
(2) Date: Jul. 7, 2022

(87) PCT Pub. No.: WO2021/140208
PCT Pub. Date: Jul. 15, 2021

(65) Prior Publication Data
US 2023/0043995 A1     Feb. 9, 2023

(30) Foreign Application Priority Data
Jan. 9, 2020     (EP) ..................................... 20150977

(51) Int. Cl.
*C12P 19/18* (2006.01)

(52) U.S. Cl.
CPC .................................... *C12P 19/18* (2013.01)

(58) Field of Classification Search
CPC ................................. C12P 19/18; C12P 19/08
See application file for complete search history.

(56) References Cited

U.S. PATENT DOCUMENTS

| | | | |
|---|---|---|---|
| 5,702,942 A | 12/1997 | Leathers et al. | |
| 6,570,065 B1 | 5/2003 | Kossmann et al. | |
| 7,182,954 B1 | 2/2007 | Cote et al. | |
| 7,402,420 B2 | 7/2008 | Kossmann et al. | |
| 9,657,322 B2 | 5/2017 | Dijkhuizen et al. | |
| 2001/0055793 A1 * | 12/2001 | Catani ..................... | C12P 19/24 |
| | | | 435/101 |
| 2009/0123603 A1 | 5/2009 | Carlson et al. | |
| 2018/0049457 A1 | 2/2018 | Cheng et al. | |

FOREIGN PATENT DOCUMENTS

| | | | | |
|---|---|---|---|---|
| CA | 3061734 A1 * | 11/2018 | .............. | C12P 19/04 |
| CN | 102459624 | 5/2012 | | |
| CN | 106661599 | 5/2017 | | |
| EP | 2084974 A1 * | 8/2009 | .............. | A23L 2/52 |
| EP | 2098127 A1 | 9/2009 | | |
| JP | 53029994 | 3/1978 | | |
| WO | 0047727 A2 | 8/2000 | | |
| WO | 2009095278 A2 | 8/2009 | | |

OTHER PUBLICATIONS

Ozturk et al., Trends in Biotechnology, 2016, (34): 4, p. 329-345 (Year: 2016).*
Joucla, Gilles: "Characterization of leuconostoc mesenteroides alternane-saccharase NRRL B-1355: rational and random approach for the design of novel glucan-saccharases", Doctoral Thesis in Biology—Health Biotechnology, (2003), Universite Paris-Est Creteil Val de Marne, [Abstract only].
Seymour, et al.: Structural Analysis of Leuconostoc Dextrans Containing 3-O-a-D-Glucosylated a-D-Glucosyl Residues in Both Linear-Chain and Branch-Point Positions, or Only in Branch-Point Positions, By Methylation and By 13C-N.M.R. Spectroscopy, Carbohydrate Research 74 (1979), pp. 41-62.
International Search Report issued in PCT/EP2021/050287 on Apr. 4, 2021.
Lopez-Munguia et al., "Production and purification of alternansucrase, a glucosyltransferase from Leuconostoc mesenteroides NRRL B-1335, for the synthesis of oligoalternans" Enzyme Microb. Technol., 1993, vol. 15, 9 pages.
Hua-Lei Chen et al., "Research on synthase appication in enzymatic synthesis" China Food Additives, 1006-2513 (2016), 11 pages.
Xu Ting, Miao Ming et al., "Optimization of the receptor reaction catalyzed by alternansucrase to produce oligosaccharide" State Key Laboratory of Food Science and Technology, 2014, 5 pages.
Chinese Office Action for Appl No. 202180008459.4 dated Apr. 3, 2024, 7 pages.
Translation of claims for JP5329994A.
English Translation of JP5329994A.
Japanese Office Action for Appl No. 2022-542403 dated Jun. 24, 2024, 4 pages.
English translation of Japanese Office Action for Appl No. 2022-542403 dated Jun. 24, 2024, 4 pages.
Nishizawa Koji et al., "Kinetic Study on Transfructosylation of B-Fructofuranosidase from Aspergillus niger ATCC 20611 and Availability of a Membrane Reactor for Fructooligosaccharide Production" Food Sci. Technol. Res., 7 (1), 39-44, 2001.

* cited by examiner

*Primary Examiner* — Robert B Mondesi
*Assistant Examiner* — Naghmeh Nina Moazzami
(74) *Attorney, Agent, or Firm* — K&L Gates LLP

(57) ABSTRACT

A process (S1) for producing alternan-oligosaccharide (8), comprising
contacting in a reactor (11) sucrose (9) with a catalytically effective amount of alternansucrase enzyme (13) and acceptor molecules (12), wherein the alternansucrase enzyme (13) and acceptor molecules (12) are present in the reactor (11) in an aqueous liquid (4) and the sucrose (9) is continuously or half-continuously fed to the reactor (11), and wherein the sucrose (9) and the acceptor molecules (12) are converted to alternan-oligosaccharide (8), and fructose (6) is formed as a by-product,
continuously or half-continuously removing at least a part of the fructose (6) from the reactor (11) by membrane filtration (17).

19 Claims, 5 Drawing Sheets

Prior art:

Invention:

Prior art:

Invention:

PROCESS FOR PRODUCING ALTERNAN-OLIGOSACCHARIDE

CROSS REFERENCE TO RELATED APPLICATIONS

This application is a national phase under 35 U.S.C. § 371 of International Application No. PCT/EP2021/050287 filed Jan. 8, 2021, which claims the benefit of priority from European Patent Application No. 20150977.5 filed Jan. 9, 2020. The entire contents of these applications are incorporated herein by reference in their entirety.

FIELD OF THE INVENTION

The present invention relates to a process for producing alternan-oligosaccharide.

BACKGROUND OF THE INVENTION

Alternan-oligosaccharides have been described as prebiotic ingredients. U.S. Pat. No. 7,182,954 discloses that oligosaccharides produced by an alternansucrase enzyme catalyzed reaction of sucrose with various acceptor sugars are effective as prebiotics for controlling enteric bacterial pathogens. Populations of enteropathogenic bacteria may be substantially reduced or inhibited by treatment of an animal with a composition comprising one or more of these oligosaccharides in an amount effective to promote the growth of beneficial bacteria (e.g. Lactobacilli, Bifidobacteria).

In WO0047727 A2 nucleic acid molecules encoding an alternansucrase are provided. Moreover, vectors, host cells and plant cells transformed by the described nucleic acid molecules and plants containing them are provided. Furthermore, methods are described for preparing transgenic plants which synthesize the carbohydrate alternan, because of the insertion of nucleic acid molecules encoding an alternansucrase. Moreover, methods for preparing alternan and products resulting from them are provided.

WO2009095278 A2 is directed to the use of an alternan polysaccharide and alternan oligosaccharide as ingredient for acidic foodstuffs and to an acidic foodstuff comprising alternan as ingredient. The disclosure is also directed to the use of alternan as a heat stable ingredient in a foodstuff formulation, and to a foodstuff comprising alternan as ingredient, wherein the foodstuff was subjected to a heating step during its manufacture.

In WO0047727 A2 and WO2009095278 A2 suggest to produce alternan-oligosaccharides by a method, wherein a) a sucrose containing solution is contacted with a catalytically effective amount of alternansucrase enzyme and acceptor molecules under conditions permitting the conversion of sucrose to alternan-oligosaccharide and fructose; and b) alternan-oligosaccharide and fructose are isolated from the solution.

The reaction is conducted in a batch reactor comprising all educts and may be conducted between room temperature and 37° C. and at a pH between about 4.7 and 7, and may be allowed to proceed until the sucrose has been essentially consumed. The product is usually obtained as a syrup which may further be purified, i.e. by membrane filtration, and/or dried.

Accumulation of-by-product is a problem of this process. Moreover, in the preparation of longer-chain maltose alternan oligosaccharides the process used hitherto can not be used, since the desired average chain lengths can not or hardly be achieved.

OBJECT OF THE INVENTION

The object of the invention was to provide an alternative process for producing alternan oligosaccharide. Preferably, the process should minimize by-products and/or allow better removal of by-products.

SUMMARY OF THE INVENTION

The invention provides a process of claim 1.

The invention provides a process for producing alternan-oligosaccharide, comprising contacting in a reactor sucrose with a catalytically effective amount of alternansucrase enzyme and acceptor molecules, wherein the alternansucrase enzyme and acceptor molecules are present in the reactor in an aqueous liquid and the sucrose is continuously or half-continuously fed to the reactor, and wherein the sucrose and the acceptor molecules are converted to alternan-oligosaccharide, and fructose is formed as a by-product, continuously or half-continuously removing at least a part of the fructose from the reactor by membrane filtration.

By the present invention, in its general form or in specific embodiments, one or more of following benefits can be reached:

A constant low fructose concentration can be reached.

The formation of further unwanted by-products, such as alternan polymer, or leucrose, can be reduced or minimized.

Fructose is not necessarily the only by-product. Further possible ones are mentioned alternan polymer or leucrose, which can also be removed, as further described below.

Longer chain alternan-oligosaccharides can be produced than in previous processes. By the amount of added sucrose, the chain length can be adjusted.

The invention provides an alternan-oligosaccharide obtained by the process.

Further benefits are mentioned in specific embodiments in the detailed description.

DETAILED DESCRIPTION

Alternan-oligosaccharide:

A degree of polymerization, DP, or an average degree of polymerization, which is the weight average degree of polymerization DPw, is determined with GPC-RI (gel permeation chromatography with refractive index detection), or with HPAEC-PAD (High performance anion exchange chromatography with pulsed amperometric detection), as alternative methods.

Alternan is a saccharide composed of glucose units, or substantially composed of glucose units in case that an acceptor molecule is present that comprises a structure other than glucose or glucose unit(s). The glucose units are linked to each other via □-1-3- and □-1-6-glycosidic bonds (also called linkages), and said two types of bonds predominantly appear alternatingly. If an acceptor molecule is present which comprises glucose (unit(s)), such as maltose, these may be linked otherwise. Alternan may contain branches (Seymour et al., Carbohydrate Research 74, (1979), 41-62). Alternan-polysaccharide and alternan-oligosaccharide are types of alternan which are distinguished by their degree of polymerization. Alternan-polysaccharide molecule may comprise an acceptor molecule or not, preferably it comprises an acceptor molecule.

Alternan in the present invention, particularly alternan-oligosaccharide, may be defined as a glucose-based saccharide, wherein said saccharide has a reducing end and D-glucose monomers linked with alternating □□1-6 and □□1-3 glycosidic linkages, wherein an acceptor molecule, also called "an acceptor molecule unit", particularly a maltose unit, is present at an reducing end, or in other words linked to an reducing end.

An alternan-oligosaccharide molecule preferably comprises one acceptor molecule.

Alternan-oligosaccharide of the invention, produced by the method of the invention preferably has a weight average degree of polymerization DPw in the range of 5-30, preferably 5-25, more preferably 10-30, or 10-20, still more preferably 10-18 or 12-18. Further preferred ranges of DPw are 18-30, or 20-30. These values are measured with GPC-RI. A detailed method description is given in the examples section.

Alternan-oligosaccharide of the invention, produced by the method of the invention preferably has an average degree of polymerization DPw in the range of 7-32, 12 to 30, 12 to 20, or 12 to 18, measured with HPAEC-PAD. A detailed method description is given in the examples section. The average degree of polymerization may be greater than 13, 14, 15, or 16 (HPAEC-PAD). In some embodiments, the average degree of polymerization is greater than 17 (HPAEC-PAD). The average degree of polymerization may be less than 20, 19, or 18 (HPAEC-PAD).

Above mentioned GPC-RI values and HPAEC-PAD values are to be seen independently from each other. This means that the values and ranges given above are not allocated to each other when comparing different methods. It is possible to produce products with different DPw, or to steer the DPw, and to measure DPw of different products with different methods.

In the invention the singular-term "alternan-oligosaccharide" designates both monodisperse alternan-oligosaccharides with molecules of only one degree of polymerization (DP) as well as polydisperse alternan-oligosaccharides with molecules having different degrees of polymerization.

Alternan-oligosaccharide of the invention preferably consists of alternan molecules having a degree of polymerization (DP) in the range of 3-30, or alternan-oligosaccharide substantially comprises or substantially consists of alternan molecules having a degree of polymerization (DP) in the range of 3-30. The DP endpoints of these ranges do not mean average values but single values.

The term "substantially comprises or substantially consists" means an amount of more than 90.0 percent by weight based on the total weight of alternan-oligosaccharide, particularly on a dry basis, preferably an amount of more than 95.0 percent by weight, or 97.0 percent by weight, more preferably more than 98.0 percent by weight, still more preferably more than 99.0 percent by weight, most preferably more than 99.5 percent by weight of alternan molecules having a degree of polymerization (DP) in the range of 3-30. In alternan-oligosaccharide minor amounts of alternan molecules with a DP of higher than 30 might be present. The term "minor amounts" means an amount of less than 10.0 percent by weight, or less than 5.0 percent by weight based on the total weight of alternan-oligosaccharide, preferably an amount of less than 3.0 percent by weight, more preferably less than 2.0 percent by weight, still more preferably less than 1.0 percent by weight, most preferably less than 0.5 percent by weight.

The degree of polymerization (DP) of alternan-oligosaccharide is defined as the number of D-glucosyl units directly or indirectly connected to the acceptor molecule plus the number of monosaccharide units of the acceptor molecule which is/are still present in the alternan-oligosaccharide.

Alternan-polysaccharide according to the definition of the invention has a DP of higher than 30. This DP does not mean an average value but a single value. In the invention the singular-term "alternan-polysaccharide" designates both monodisperse alternan-polysaccharides with molecules of only one degree of polymerization (DP) as well as polydisperse alternan-polysaccharides with molecules having different degrees of polymerization.

Alternan-polysaccharide according to the definition of the invention may have a weight average molecular weight Mw of more than 5000 g/mol (determined with GPC RI or GPC MALLS). In another embodiment, alternan-polysaccharide has a weight average molecular weight Mw in the range of 10000000 g/mol to 60000000 g/mol (determined with GPC MALLS), more preferably in the range of 12000000 g/mol to 50000000 g/mol.

Alternansucrase Enzyme:

Alternansucrase for use herein may be obtained from a variety of microorganisms, preferably strains of Leuconostoc and particularly strains of *L. mesenteroides*, as for example disclosed in WO 00/47727. In one embodiment, the enzyme is produced by strains of which secrete a high proportion of alternansucrase to dextransucrase such as described by Leathers et al., U.S. Pat. No. 5,702,942. In another embodiment the alternansucrase enzymes that can be used to produce alternan-oligosaccharides include Leuconostoc mesenteroides strains NRRL B 1355, 23185, 23186, 23188, 23311, 21297, 30821, 30894 These enzymes can be additionally cloned and expressed recombinantly, such as described in Gilles Joucla, Doctoral Dissertation, Ingenier INSA, Toulouse, France, 2003. Alternansucrase enzyme can be produced in an organism other than *L. mesenteroides*, the organism comprising a recombinant nucleic acid encoding the Alternansucrase enzyme. A preferable organism is *E. coli*.

Production of the alternansucrase may be conducted by culture of any of the above-mentioned microorganisms using conventional techniques and under aerobic conditions which are effective to promote growth and production of the enzyme such as described in Leathers et al. Following culture, the enzyme may be isolated or separated from the microorganisms using conventional techniques, such as by centrifugation or filtration.

In one embodiment the term that "the alternansucrase enzyme is present in the reactor in an aqueous liquid" means that alternansucrase enzyme is dissolved, emulsified or suspended in the aqueous liquid, preferably dissolved. In one embodiment, alternansucrase enzyme is not immobilized on a carrier material.

Acceptor Molecule:

The acceptor molecule is understood to mean a molecule at which an alternansucrase is able to catalyze a chain-extending reaction. An alternan-oligosaccharide molecule comprises an acceptor molecule, preferably one acceptor molecule. An alternan-polysaccharide molecule preferably comprises an acceptor molecule, more preferably one acceptor molecule. Even when the singular term molecule is used, a plurality of acceptor molecules is used in the invention, wherein these can be chemically identical or different.

Alternan, particularly alternan-oligosaccharide, can be produced from an acceptor molecule and sucrose that are reacted with one or more alternan sucrase enzymes that will transfer glucose units from sucrose to an acceptor molecule and will release fructose and alternan, particularly alternan oligosaccharide. An acceptor molecule can accept a glucose unit from sucrose.

The acceptor molecule which can be added to the reaction mixture is preferably a carbohydrate or a carbohydrate derivative. The use of external acceptors leads to the production of low molecular alternan-oligosaccharides. An acceptor molecule may be selected from a sugar or sugar alcohol having free hydroxyl groups at one or more of carbon positions numbers 2, 3 and 6 that can accept a glucose unit from sucrose.

The carbohydrate acceptor is preferably a saccharide selected from the group consisting of maltose, isomaltose, maltitol, (iso)maltotriose and methyl-□-D-glucan. Other preferred acceptor molecules are glucose, gentiobiose, raffinose, melibiose, isomaltitol, isomaltooligosaccharide, theanderose, kojibiose, glucosyl trehaloses, cellobiose, maltotetraose, nigerose, lactose, panose or mixtures thereof. The acceptor molecule is preferably maltose.

Depending upon the particular acceptor selected, the glucosyl units will generally be added through an $\alpha(1,6)$ linkage, or through an $\alpha(1,3)$ linkage if an $\alpha(1,6)$ linkage is already present. The reaction will typically produce a mixture of oligosaccharides having different degrees of polymerization (DP).

In one embodiment the term that the "acceptor molecule is present in the reactor in an aqueous liquid" means that acceptor molecule is dissolved, emulsified or suspended in the aqueous liquid, preferably dissolved.

Aqueous Liquid:

The term "aqueous liquid" in this invention means a liquid comprising at least 80 vol. % of water, preferably at least 90 vol. % of water, or at least 95 vol. %. An upper limit is 100 vol. %. Preferably, the aqueous liquid is water.

Reactor:

The reactor may be a tank reactor.

The reaction may be done under agitation, such as stirring. In one embodiment, the reactor is a stirred tank reactor. In another embodiment, that could be combined with the previous, agitation is done by moving the content of the reactor, preferably by pumping, preferably by circulation of the content of the reactor by a pump as described elsewhere in this specification.

When agitation is done, particularly stirring, the
contacting in a reactor sucrose with a catalytically effective amount of alternansucrase enzyme and acceptor molecules, wherein the alternansucrase enzyme and acceptor molecules are present in the reactor in an aqueous liquid and the sucrose is continuously or half-continuously fed to the reactor,
is done with agitation, particularly stirring.

In another embodiment, removal of fructose and/or addition of sucrose causes turbulences in the reactor that cause mixing of components.

The sucrose (substrate) is continuously or half-continuously added.

The term "half-continuously" with respect to sucrose feed means that feed of sucrose is interrupted one or more times, preferably more than one time. In other words, "half-continuously" means that there are at least two time periods of feeding, preferably at least three time periods, or at least four time periods of feeding, wherein each time period of feeding is separated from a following time period of feeding by a time period of interruption of feeding. Time periods of sucrose feed may be constant time periods or nonconstant time periods (i.e. time periods may differ from each other in length). Time periods of interruption of feed may be constant time periods or nonconstant time periods. Time periods of sucrose feed and time periods of interruption of feed may be time periods of the same length or time periods of different length.

The term "half-continuously" with respect to fructose removal means that removal of fructose is interrupted one or more times, preferably more times (more than one time). In other words, "half-continuously" means that there are at least two time periods of removal (or removing), preferably at least three time periods, or at least four time periods of removal, wherein each time period of removal is separated from a following time period of removal by a time period of interruption of removal. Time periods of the fructose removal may be constant time periods or nonconstant time periods. Time periods of interruption of fructose removal may be constant time periods, or nonconstant time periods. Time periods of fructose removal and time periods of interruption of fructose removal may be time periods of the same length or time periods of different length.

In half-continuous operation, time periods where sucrose is fed and time periods where fructose is removed may be identical, overlap or not overlap. In one embodiment of half continuous operation, sucrose feed is done when fructose removal is interrupted, and sucrose feed is interrupted when fructose removal is done. This particularly means that sucrose feed and fructose removal are done alternatingly.

Feeding sucrose to the reactor can be done directly or indirectly. Direct feeding is done, for example, when sucrose or a sucrose solution is added via a supply pipe which directly ends at or in the reactor. Indirect feeding is done, for example, when sucrose or a sucrose solution is added via a supply pipe which ends at another device which is in fluid communication with the reactor, for example a further pipe, or a further device, such as a device comprising a membrane, which is mentioned herein below, or feeding may be done to a reactor system comprising the reactor and the device comprising a membrane, which is mentioned herein below. Feeding (or supply) of sucrose is not done through a membrane. I.e. in feeding of sucrose, sucrose does not penetrate a membrane. If sucrose is fed to above-mentioned device comprising a membrane the supply of sucrose is not through the membrane of the device. I.e. sucrose does not penetrate the membrane of the device. Said membrane, used in the membrane filtration for removing fructose is a membrane that lets fructose and a portion of the aqueous liquid penetrate, but not sucrose.

Catalytically effective amounts of alternansucrase enzyme and the acceptor molecules are present in the reactor before sucrose is added. Sucrose may be added as a solid or, preferably, added as solution or suspension, preferably in aqueous liquid. Supplied sucrose can directly be converted by the alternansucrase.

In the process, the bioconversion, i.e. the enzymatic formation of alternan oligosaccharides, takes place under continuous or half-continuous fructose removal. Removal is done after formation of alternan oligosaccharide has started and when fructose is produced as a by-product.

In one embodiment, removal of fructose is done at the same time when the sucrose is fed to the reactor. At the same time means that a period, or periods, of sucrose addition and a period, or periods, of fructose removal at least in part overlap. Preferably, fructose is removed at least at the whole time when sucrose is added. Fructose removal may be continued after an addition of sucrose is stopped or when addition of sucrose has ended.

Removing at least a part of the fructose is related to the whole amount of fructose formed in the process (as by product). Removing at least a part of the fructose preferably means equal or more than 70 mol % of the total fructose which is produced, preferably equal or more than 80 mol %, more preferably equal or more than 90 mol %. An upper limit of removal is 100 mol %. Preferably, the whole amount of produced fructose (100 mol %) or substantially the whole amount are removed. Substantially the whole amount means equal or more than 95 mol %.

Removal of fructose is also called depletion.

Removal of fructose is in one embodiment performed by a diafiltration. I.e. the membrane filtration is a diafiltration or performed as a diafiltration.

In one embodiment of the invention removing at least a part of the fructose comprises continuously or half-continuously circulating the content of the reactor through a device comprising a membrane and contacting the content of the reactor with the membrane, wherein at least a portion of the fructose and a portion of the aqueous liquid pass the membrane (as permeate), and wherein a remainder (a retentate) is returned to the reactor.

The term "half-continuously" with respect to circulating means that circulating is interrupted one or more times, preferably more times (more than one time). In other words, "half-continuously" means that there are at least two time periods of circulating, preferably at least three time periods, or at least four time periods of circulating, wherein each time period of circulating is separated from a following time period of circulating by a time period of interruption of circulating. Time periods of circulating may be constant time periods or nonconstant time periods. Time periods of interruption of circulation may be constant time periods or nonconstant time periods. Time periods of circulating and time periods of interruption of circulating may be time periods of same length or time periods of different length.

The temperature in the reactor is in a specific embodiment in a range of 30-45° C., or 30-40° C.

The device comprising a membrane may be a membrane cell, or a membrane module or a filtration cell comprising a membrane.

The device comprising a membrane is in fluid communication with the reactor. Content of the reactor is conducted to said device and from that device back to the reactor. But a portion of the fructose and a portion of the aqueous liquid pass the membrane (as permeate) and are not conducted back to the reactor.

The device comprising a membrane may be connected with the reactor by connections suitable for transport of liquid, such as tubings, pipes or pipelines. A first connection may be present between an reactor outlet and an inlet of the device. A second connection may be present between an outlet of the device and an reactor inlet. A pump for circulation the content of the reactor may be present. Circulating the content of the reactor is done through the reactor itself and through the membrane device. Both is also called a "reactor system", the system comprising the reactor and the device comprising a membrane. The circular flow of the reactor content may cause mixture of ingredients in the liquid phase, particularly in a turbulent flow.

In one embodiment, continuously or half-continuously removing at least a part of the fructose from the reactor is done by nano-filtration. The membrane is preferably a nanofiltration membrane.

By continuous or half-continuous circulation through a device comprising a membrane, fructose and aqueous liquid are continuously or half-continuously removed.

In one embodiment the pressure applied in membrane filtration for removing fructose is in a range of 5 to 30 bar. The temperature may be 30-40° C.

In a further embodiment, the process comprises continuously or half-continuously feeding further aqueous liquid to the reactor or to a reactor system comprising the reactor and the device comprising a membrane. By this measure, aqueous liquid which leaves the reactor or the reactor system as a part of the permeate, can be replaced. "Further aqueous liquid" means aqueous liquid that is added to the reactor in the course of the process. In other words further aqueous liquid means aqueous liquid that is added in addition to the aqueous liquid that is mentioned in claim 1. The term "half-continuously" with respect to feeding further aqueous liquid means that feeding further aqueous liquid is interrupted one or more times, preferably more times (more than one time). In other words, "half-continuously" means that there are at least two time periods of feeding, preferably at least three time periods, or at least four time periods of feeding, wherein each time period of feeding is separated from a following time period of feeding by a time period of interruption of feeding. Time periods of the feeding further aqueous liquid may be constant time periods or nonconstant time periods. Time periods of interruption of feeding further aqueous liquid may be constant time periods, or nonconstant time periods. Time periods of the feeding further aqueous liquid and time periods of interruption of feeding further aqueous liquid may be time periods of same length or time periods of different length.

In one embodiment the process further comprises removing at least a part of alternan-polysaccharide, which is formed as a by-product, and at least a part of the alternan-sucrase enzyme, which is done preferably by a further membrane filtration. Alternan-polysaccharide is formed as a further by-product, in addition to fructose, which is also a by-product of the process. This step is optionally done in order to separate by-product. In case of membrane filtration, alternan-oligosaccharide is obtained in a permeate. And alternan-polysaccharide and alternansucrase are comprised in a retentate. In one embodiment this membrane filtration is an ultra-filtration. The membrane is preferably an ultrafiltration membrane. In one embodiment the pressure applied in such membrane filtration, particularly ultrafiltration, is in a range of 2 to 15 bar. The temperature in this further membrane filtration may be in the range of 30-60° C.

The further membrane filtration (for removing at least a part of alternan-polysaccharide and at least a part of the alternansucrase enzyme) may be done with a further device comprising a membrane, which is a further membrane.

In one embodiment the process further comprises concentrating the product that is obtained after removal at least a part of alternan-polysaccharide and after removal at least a part of the alternansucrase enzyme, the product comprising alternan-oligosaccharide. Particularly the process may further comprise concentrating alternan-oligosaccharide, preferably in the permeate which is obtained in said further membrane filtration.

In the membrane filtration for removal of fructose, or in an optional further membrane filtration (for removing at least a part of alternan-polysaccharide and at least a part of the alternansucrase enzyme), a membrane of any known or usual material may be used. Non-limiting examples are polyamide, polythersulfone, or poly(vinylidene)fluoride.

In one embodiment the process further comprises drying the product which is obtained. Concentration, as mentioned before, is intended to mean that the product is still in a liquid phase. Drying means obtaining a solid product.

Preferably a product is dried that is obtained after removal at least a part of alternan-polysaccharide, which is formed as a by-product, and at least a part of the alternansucrase enzyme. Above-mentioned concentration and drying can be performed consecutively.

A dried product may comprise at least 65% (w/w), or at least 70% (w/w), or at least 75% (w/w) or at least 80% (w/w) alternan oligosaccharides on a dry basis, more specifically at least 85% (w/w) or at least 95% (w/w). A preferable upper limit that could be combined with each of the lower limits is 99.0% or 99.9% (w/w).

A dried product may comprise 0.1 to 15% (w/w), or 0.1 to 10% (w/w), or 0.1 to 9% (w/w), or 0.1 to 8% (w/w), or 0.1 to 7% (w/w), or 0.1 to 6% (w/w), or 0.1 to 5% (w/w) or 0.1 to 3% (w/w), or 0.1 to 2% (w/w), or 0.1 to 1% (w/w), or 0.1 to 0.5% (w/w) of fructose equivalents on a dry basis. In some embodiments, a dried product comprises less than 10% (w/w) of fructose equivalents on a dry basis. Preferably, said composition comprises less than 9% (w/w), less than 8% (w/w), less than 7% (w/w), less than 6% (w/w), less than 5% (w/w) less than 3% (w/w), less than 2% (w/w), less than 1% (w/w), or less than 0.5% (w/w) of fructose equivalents on a dry basis.

In some embodiments, said fructose equivalents are leucrose, fructose and/or sucrose. In some embodiments, said fructose equivalents are leucrose. In some embodiments, said fructose equivalents are fructose. In some embodiments, said fructose equivalents are sucrose. In some embodiments, said fructose equivalents are leucrose and fructose. In some embodiments, said fructose equivalents are leucrose and sucrose. In some embodiments, said fructose equivalents are fructose and sucrose. In some embodiments, said fructose equivalents are leucrose, fructose, and sucrose.

Fructose equivalents which are a by-product of the process can be removed in the process. This was already described with respect to fructose. In one embodiment the process comprises continuously or half-continuously removing at least a part of leucrose, formed as a by product, from the reactor by membrane filtration. The membrane filtration is preferably the same that is used for removal of fructose. So, fructose and leucrose can be removed in the same membrane filtration step.

Fructose equivalents which belong to an educt of the process can be removed in the process. In one embodiment the process comprises continuously or half-continuously removing at least a part of sucrose, as non-reacted educt, from the reactor by membrane filtration. The membrane filtration may be the same that is used for removal of fructose. So, fructose and sucrose can be removed in the same membrane filtration step.

In one embodiment of the process, an average degree of polymerization DPw or DPn of the alternan-oligosaccharide is regulated by the amount of the sucrose which is fed to the reactor.

In a further embodiment, feeding of the sucrose is stopped when a desired average degree of polymerization DPw or DPn of the alternan-oligosaccharide is, or has been, reached.

After stopping the addition of sucrose the removal of fructose may be continued until a desired fructose concentration is, or has been, reached.

By the amount of added sucrose, the chain length produced can be adjusted. The extent of the degree of polymerization may vary with the concentrations and the relative ratio of sucrose and acceptor molecules. The reaction product will generally be composed of a mixture of alternan oligosaccharides having different degrees of polymerization. At a relatively high sucrose:acceptor ratio, more glucosyl units are transferred into glucan and products with higher degree of polymerization are obtained (i.e. the relative amounts of the high DP oligosaccharides in the product will be increased). In contrast, at a low sucrose:acceptor ratio, the predominant reaction product is that resulting from the transfer of a single glucosyl unit to the acceptor.

Thus, the yields of oligosaccharides of a desired degree of polymerization may be optimized by varying the sucrose:acceptor ratio (also named sucrose to acceptor ratio).

The sucrose:acceptor molecules-ratio means the total amount of sucrose added during the process in relation to the total amount of acceptor molecules used in the process. This ratio may be given in a mass ratio or in a molar ratio.

An actual ratio in the reactor is lower than mentioned ratio, because sucrose is fed continuously or half-continuously and not at once and because fed sucrose is consumed.

The sucrose:acceptor molecules-ratio in terms of mass ratio (for example kg sucrose:kg acceptor molecules) is preferably in the range of 10:1-30:1, more preferably 15:1-23:1. The acceptor molecules are preferably maltose, but other acceptors may be applied also with this range.

The sucrose:acceptor molecules-ratio in terms of molar ratio (for example Mol sucrose molecules:Mol acceptor molecules) is preferably in the range of 10:1-30:1, more preferably 15:1-23:1, wherein the acceptor molecules are preferably maltose, but other acceptors may be applied also with this range.

A feed rate or feed modus, e.g. continuously or half-continuously, of sucrose is preferably chosen in such a manner that the concentration of fructose in the reactor does not increase during the process or in a manner that fructose is not accumulated.

A feed rate of sucrose is preferably chosen in such a manner that the concentration of sucrose in the reactor does not increase during the process or in a manner that sucrose is not accumulated. The feed rate is preferably chosen in such a manner that fed sucrose is directly consumed in the reaction.

A preferable feed rate of sucrose is 50-1500 g/h, or 50-1000 g/h, or 50-800 g/h, or 50 g/h-500 g/h, or 50 g/h-250 g/h, or 50 g/h-200 g/h, or the respective rate in expressed in mol/h (molar mass of sucrose 342.30 g/mol). When sucrose is added in solution or suspension, this rate means the weight of sucrose only, not the weight of the whole solution or suspension.

In one embodiment of the process, further alternansucrase enzyme is fed to the reactor, preferably continuously or half-continuously. So, further alternansucrase enzyme is added to the alternansucrase enzyme that was present before in the reactor (the alternansucrase enzyme mentioned in claim 1). By this measure, higher total units of alternansucrase enzyme activity can be reached, and the reaction time can be reduced. Preferably, sucrose amount is adapted to the higher total units of enzyme, by also increasing the sucrose amount.

The term "half-continuously" with respect to alternansucrase enzyme-feed means that feed of enzyme is interrupted one or more times, preferably more than one time. In other words, "half-continuously" means that there are at least two time periods of feeding, preferably at least three time periods, or at least four time periods of feeding, wherein each time period of feeding is separated from a following time period of feeding by a time period of interruption. Time periods of enzyme feed may be constant time periods or nonconstant time periods (i.e. time periods may differ from each other in length). Time periods of interruption of feed may be constant time periods or nonconstant time periods. Time periods of enzyme feed and time periods of interruption of feed may be time periods of the same length or time periods of different length.

A preferable ratio of alternansucrase enzyme:sucrose (the total amount of fed sucrose) is 1000-10000 units (enzyme activity):1000 g of sucrose, or 1000-7000 units (enzyme activity):1000 g of sucrose, or 1000-5000 units (enzyme activity):1000 g of sucrose, or 1000-2500 units (enzyme activity):1000 g of sucrose, preferably 1200-2300 units (enzyme activity):1000 g of sucrose, more preferably 1500-2000 units (enzyme activity):1000 g of sucrose. These ratios are related to the total units of alternansucrase enzyme activity. The units (enzyme activity) mean the total units of alternansucrase enzyme used in the process. If, for example, further alternansucrase enzyme is fed to the reactor, the sum of (i) alternansucrase enzyme that is present at the beginning and (ii) all alternansucrase enzyme that is further fed to the reactor means the total units.

With mentioned parameters it is particularly possible to reach preferable DPw or DPn of oligosaccharide, some of which are mentioned here in the description.

The reaction time, related on the process of claim 1, can depend on the chosen sucrose:acceptor ratio, the chosen feed rate of sucrose, the chosen enzyme activity, and/or the chosen total amount of sucrose. Typical times are in the range of 10-150 h, or 10-30 h, or 10-24 h, or 10-20 h. Further process steps like removing alternan-polysaccharide, which is formed as a by-product, and alternansucrase enzyme by a further membrane filtration, or concentrating a retentate which is obtained in the further membrane filtration, which are mentioned elsewhere, are not included.

The reaction temperature, related on the process of claim 1, is preferably in the range of 30-60° C. Specific temperature ranges or different temperatures may be applied in different process phases or steps.

In one embodiment, the sucrose is continuously fed and a feed rate of sucrose, in molar amount of sucrose per time, is equal or substantially equal to a rate of continuous removal of fructose, in a molar amount of fructose per time, or the ratio of the rate of feed of sucrose to the rate of removal of fructose is in the range of 1.2:1 to 1:1. Per molar amount of sucrose that is consumed in alternan-oligosaccharide formation the same molar amount of fructose is produced, and it is preferred to remove the said molar amount continuously.

Hereinafter, the invention is exemplified by examples which are not to be construed as a limitation of the general idea of the invention as described before and laid down in the claims.

EXAMPLES

Methods
Determination of DP with HPAEC-PAD

Values for DP were measured by HPAEC-PAD after reducing and hydrolyzing glucose-based saccharides. Two milliliters of a solution containing 6 g/mL of digestible carbohydrate composition were treated with 0.2 mL of a $NaBH_4$ solution (40 mg/mL) in 0.5 M ammonia at 40° C. for 30 min. Reduced samples were subsequently hydrolyzed with 0.5 mL 2 M Trifluoroacetic acid heated at 121° C. for 1 h to release monomers. The released monomers were quantified by injecting sample solutions on a Thermo Scientific™ Dionex™ ICS-6000 ion chromatograph system equipped with a CarboPac™ MA1 and fed with eluents (water and NaOH 1000 mM) at 0.4 mL/min. DP values are calculated with the following formula:

$$DP = \frac{\left(\frac{\text{sugar alcohols}}{182}\right) + \left(\frac{\text{glucose content}}{180}\right)}{\left(\frac{\text{sugar alcohols}}{182}\right)}$$

Determination of DP with GPC-RI

Values for DP were alternatively measured by GPC-RI. Samples were diluted with water and subjected to gel permeation chromatography in water (0.5 mL/min) using 2×Tosoh TSK GEL G2500 PWXL columns coupled in series. Oligosaccharides are separated during permeation by their relative molecular weight and quantified using refractometric detection. Molecular weight quantification was based on the external standard approach using standards ranging from 342 to 5000 Da (PSS-Polymer Standards). The Chromeleon Extension Pack V2.0 was used according to Dionex instructions for calibration and calculation.

WORKING EXAMPLES

Example 1

Figure 1A:
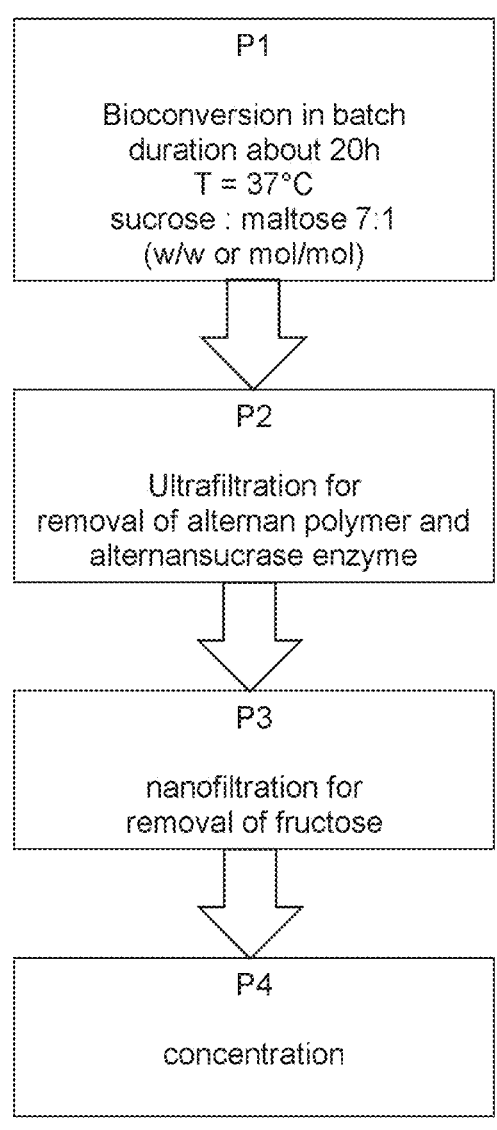
FIG. 1a shows a scheme of the process according to the prior art.
Figure 2A:
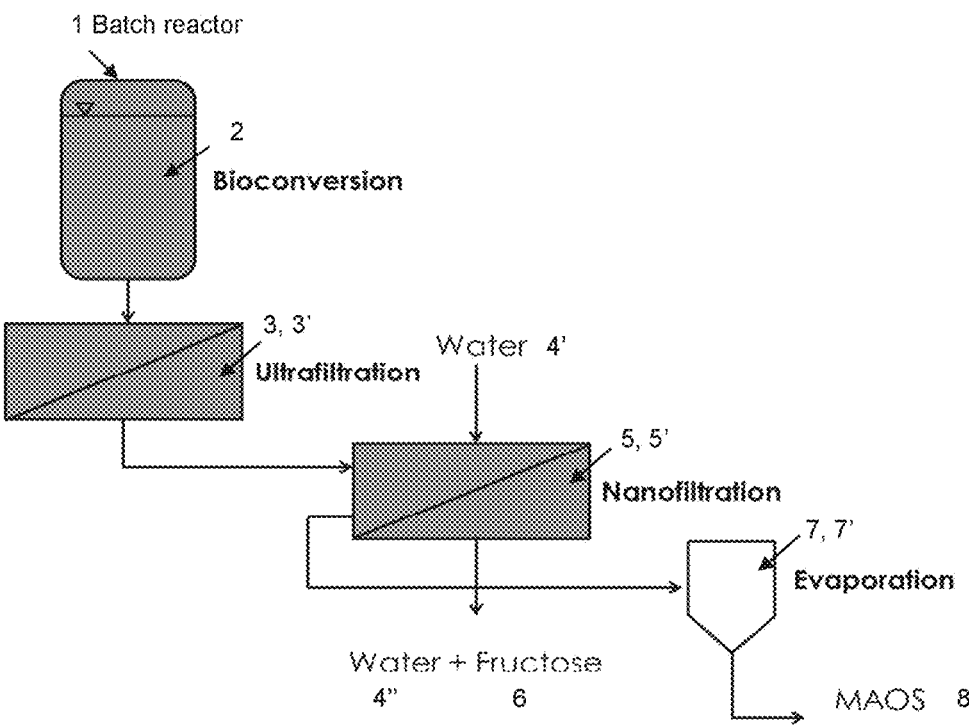
FIG. 2a shows a process design of the prior art process.

The prior art process is known for example from WO 0047727 A2 and WO 2009095278 A2, and comprises following four steps P1-P4 of FIG. 1a:

In step P1 bioconversion 2 of sucrose and maltose is done in in batch reactor 1 for a duration of about 20 h at T=37° C. The sucrose:maltose ratio is chosen to 7:1 (w/w or mol/mol). Step P1 is done in the batch reactor 1 for bioconversion 2 which is shown in FIG. 2a.

P2 is a step of ultrafiltration 3 for removal of alternan-polymer (alternan polysaccharide) and alternansucrase enzyme (AlSu). This step is done in the ultrafiltration device 3' shown in FIG. 2a.

In P3, fructose is removed by nanofiltration 5. This step is done in the nanofiltration device 5' shown in FIG. 2a. Here, water 4' is added and a mixture of water 4'' and fructose 6 is removed.

In the final step P4 the product from P3 is concentrated by evaporation 7. This is done in the evaporation device 7' in FIG. 2a and maltose-alternan oligosaccharide (MAOS) 8 is obtained.

Figure 1B:
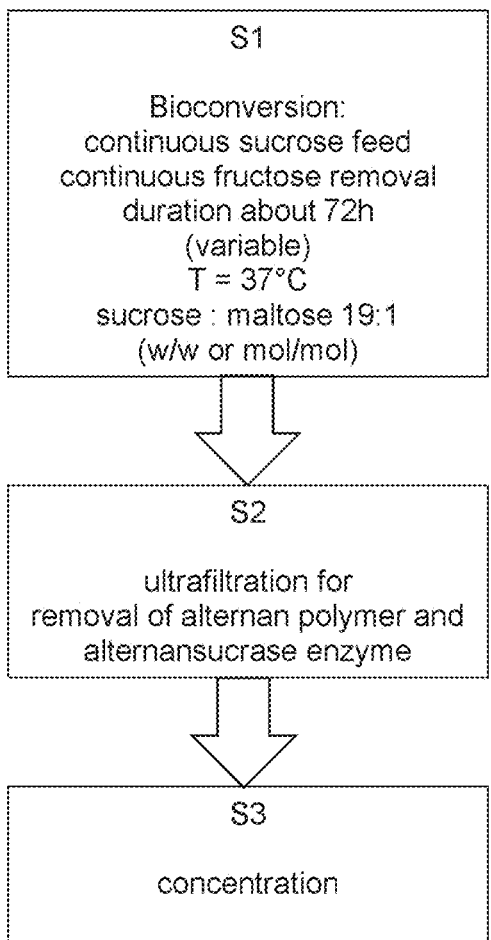
FIG. 1b shows a scheme of the process of the invention.

The process of the invention, in a specific embodiment, comprises three steps S1-S3, shown in FIG. 1b:

In comparison to the prior art process of FIG. 1a, the bioconversion 2 in step S1 comprises continuous feed 10 of sucrose 9 and continuous removal of fructose 6. Half-continuous feed and removal is possible. The mass ratio of sucrose 9 (total amount added) to maltose 12 is 19:1 (19 kg sucrose per 1 kg maltose) and the duration is about 72 h. Step P3 of the prior art can be omitted because fructose 6 is removed in step S1 already. Removing fructose 6 makes possible using a higher ratio of sucrose 9 to maltose 12 and reaching a higher degree of polymerization of the maltose-alternan-oligosaccharide 8.

Figure 2B:
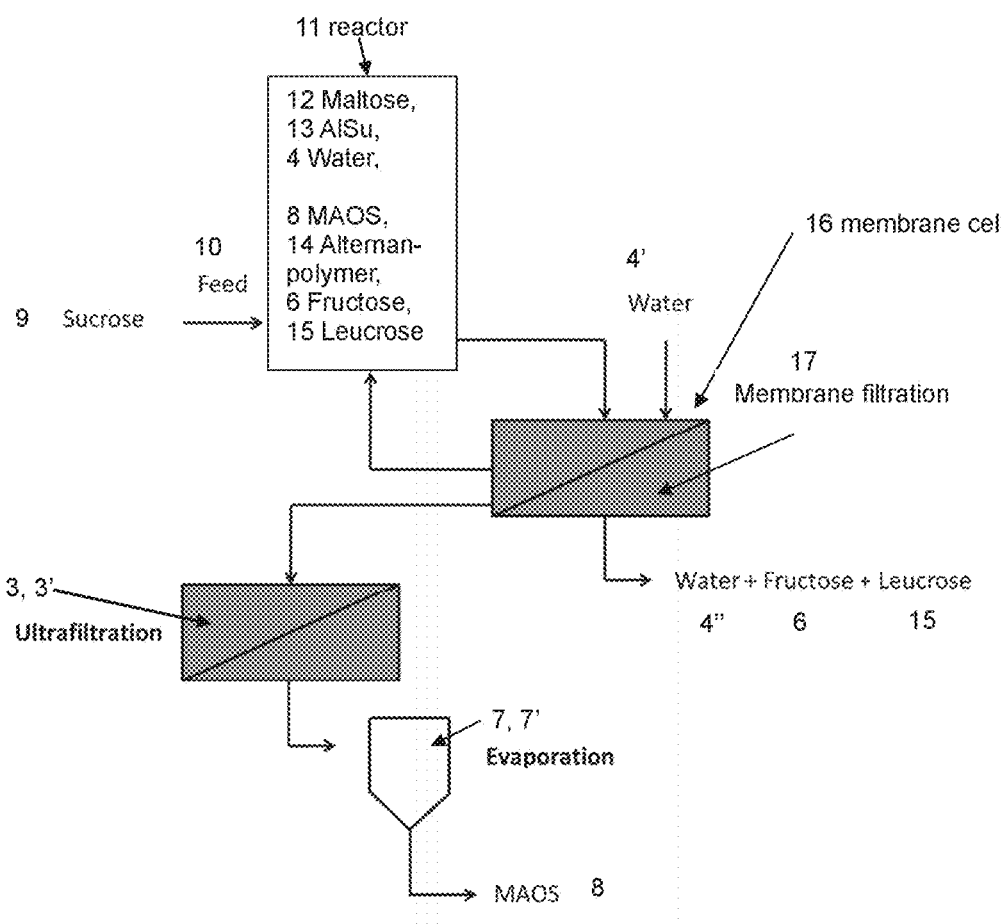
FIG. 2b shows a process design of the process of the invention.

Step S1, a bioconversion, is done in the reactor 11 in FIG. 2b, wherein maltose 12 and alternansucrase enzyme (AlSu) 13 are present in water 4. A stated above, bioconversion is done with continuous feed 10 of sucrose 9, continuous removal of fructose 6, for a duration about 72 h (variable), T=37° C., and a sucrose:maltose ratio of 19:1 (w/w or mol/mol). Sucrose 9 is added as feed (dissolved in water) 10 and the reactor 11 content is stirred. In the bioconversion in the reactor 11, alternan oligosaccharide comprising acceptor molecule maltose, also called maltose alternan oligosaccharide 8 (MAOS), is formed as main product and alternan polymer 14, fructose 6 and leucrose 15 are formed as by-products. Content from the reactor 11 is continuously circulated through the membrane cell (diafiltration cell) 16, where water 4", fructose 6 and leucrose 15 are removed in membrane filtration 17, which in this example is a nanofiltration, done as a constant volume diafiltration. Leucrose 15 content is reduced from about 30% to less than 10%, in comparison with the prior art. Removed water 4" is replaced by the water 4' feed stream.

The reactor 11 and the membrane cell 16 form a combined bioconversion and nanofiltration device, also called reactor system.

Process step S2 of this embodiment corresponds to step P2 of the prior art. Here, alternan polysaccharide (alternan polymer) 14, as by product, and alternansucrase enzyme (AlSu) 13 are removed by ultrafiltration 3 in device 3'. The step is beneficial in case that more alternan polymer 14 as desired has been formed, or in order to steer desired DPw of the alternan species remaining.

Process step S3 of this embodiment corresponds to step P4 of the prior art. Here the product is concentrated by evaporation 7 in device 7'.

The composition of the reaction solution used during the production is shown in Table 1. The 2.1 L solution gives a total of about 5.6 L with the water in the system (dead volume).

The process is run without depletion for the first hour to minimize potential loss of maltose across the membrane. Subsequently, fructose is constantly depleted via a nanofiltration membrane Filmtec NF270-2540 (DOW). Upon completion of the chain extension, the nanofiltration module was replaced with a TRISEP 2540-UE50-QXF ultrafiltration module (Microdyn Nadir). This separated the maltose-alternan oligosaccharide (MAOS) fraction from the longer aging chains and the enzyme. The membranes used during the process and process parameters used are summarized in Table 2. The filtrate was finally concentrated to a dry matter content of >72%.

TABLE 1

| Composition of the reaction solution | | |
| --- | --- | --- |
| Component | Amount | feed rate |
| maltose | 451 g | Batch |
| sucrose | 8500 g | ~100 g/h |

TABLE 1-continued

| Composition of the reaction solution | | |
| --- | --- | --- |
| Component | Amount | feed rate |
| sodium acetate | 57 g | Batch |
| alternansucrase | 1900 U | Batch |
| water | ad 2.1 L | Batch |

TABLE 2

| membranes and parameters | | | |
| --- | --- | --- | --- |
| process step | filter | pressure | temperature |
| nanofiltration | Filmtec NF270-2540 (DOW) | 5-30 bar, actually used 15 bar | 30-40° C., actually used 37° C. |
| ultrafiltration | TRISEP 2540-UE50-QXF (Microdyn Nadir) | 2-15 bar, actually used 10 bar | 30-60° C., actually used 40° C. |

Figure 3:
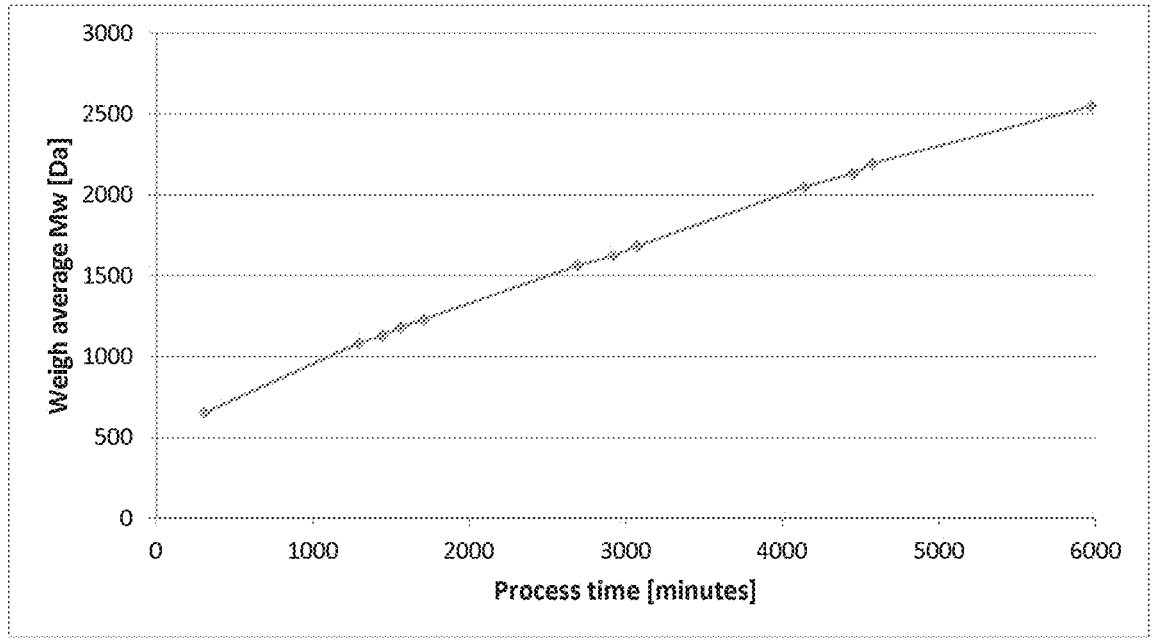
FIG. 3 is a chart showing the increase of molecular weight over the process time when constant feed of sucrose is applied.

FIG. 3 shows the increase in chain length over the course of the process. The values were recorded by GPC-RI measurements. The relationship for calculation of DPw from the Mw values of FIG. 3 is as follows: DPw=Mw/(162 Da). So it can be seen that at the end of the process, a DPw of about 15.4 is reached (2500/162).

In order to reach an average chain length DPw of about 15, 19 kg of sucrose (in total) were used per 1 kg of maltose.

Comparative Example

Alternan-oligosaccharide was made according to a process as shown in FIG. 1a. A ratio of 21:1 (kg Sucrose:kg Maltose) was used and a DPw of 9.9 was obtained. For the measurement of DPw, GPC-RI was used, but not exactly according to the method-protocol as mentioned above in the method section. Nevertheless, in comparison with the results of FIG. 3 it is shown that by the present invention alternan with higher DPw can be obtained.

DPw values for two samples obtained by the method of the invention that were analyzed with HPAEC-PAD method are summarized in the table 3 below:

TABLE 3

| Tested Product | Avg DP (DPw) |
| --- | --- |
| Comparative Sample DCC-1 | 6.9 ± 0.02 |
| Sample DCC-2 | 12.4 ± 0.24 |
| Sample DCC-3 | 17.3 ± 0.53 |
| P2 | |

Samples DCC-2 and DCC-3 were produced by a process of the invention.

Glycosidic linkage profiles for glucose-based oligosaccharides were measured with partially-methylated alditol acetates by GC-MS. Briefly, samples were dissolved in anhydrous DMSO, deprotonated by an addition n-Butyl Lithium (Sigma 230707) and methylated with Methyl iodide (Sigma 289566). The methylated samples were subsequently hydrolyzed with 2 N TFA (60 min at 121° C.). The hydrolyzed samples were evaporated under a nitrogen air draft, re-dissolved in 1 M ammonium hydroxide and aldehyde groups were reduced with a DMSO solution containing sodium borodeuteride (20 mg/ml). Glacial acetic acid was added drop wise to stop reaction and acetylation was done by addition of 1-methylimidazole and acetic anhydride. Partially methylated alditol acetates in acetone were quantified by GC-MS (7890A-5975C MSD, Agilent Technologies, Inc., Santa Clara, CA, USA) using a Supelco 24111-U SP-2380 capillary column (injector volume, 0.5 µl; injector temperature, 250° C.; detector temperature, 250° C.; carrier gas, helium: 30 mL/min; split ratio, 40:1; temperature program, 100° C. for 3 min, 4° C./min to 270° C. for 20 min. Electron impact spectra were acquired at 69.9 eV over 50-550 Da mass range.

| Glycosydic-linkage | DCC-1 | DCC-2 | DCC-3 |
|---|---|---|---|
| Terminal-Glc | 36 | 31.5 | 29.3 |
| 1,3-D-Glc | 13 | 15.2 | 16.8 |
| 1,6-D-Glc | 39 | 44.1 | 44.3 |
| 1,4-D-Glc | 11 | 6.8 | 5.0 |
| 1,3,6-D-Glc | 1.4 | 2.4 | 4.7 |

Higher values of 1,6-glycosidic linkages are explained by the leucrose content in the digestible carbohydrate compositions that contributes to the amounts of 1,5,6-Tri-O-acetyl-1-deuterio-2,3,4-tri-O-methyl-D-glucitol observed. In addition, leucrose, as well as monomeric glucose, contributes to the amounts of terminal-Glc in the digestible carbohydrate compositions.

Example 2

In this example, parameters were varied as shown in the following table and alternansucrase was given to the reactor in 4 equal portions, the first portion being present before sucrose was fed to the reactor.

| Parameter | 1. experiment-72 h process | 2. experiment -24 h process |
|---|---|---|
| Sucrose amount | 15.5 kg | 16.5 kg |
| Feeding rate | 250 g/h | 775 g/h |
| Enzyme activity | 56 kU | 79.2 kU |
| Temperature | 37° C. | 43° C. |
| Time | 72 h | 27 h |

Reaction time of the process of the invention (not including here further process steps like removing alternan-polysaccharide and alternansucrase enzyme by a further membrane filtration, or concentrating a retentate which is obtained in the further membrane filtration) could be reduced by increasing the sucrose amount, increasing the sucrose feeding rate, increasing the enzyme activity and increasing the temperature.

LIST OF REFERENCE SYMBOLS

P1 Bioconversion in batch
P2 ultrafiltration
P3 nanofiltration
4 concentration
S1 Bioconversion
S2 ultrafiltration
S3 concentration
1 batch reactor
2 bioconversion
3 membrane filtration, in the example: ultrafiltration
3' membrane filtration device, in the example: ultrafiltration device
4 aqueous liquid, in the example: water 4' aqueous liquid, in the example: water
4" aqueous liquid, in the example: water
5 nanofiltration
5' nanofiltration device
6 fructose
7 evaporation
7' evaporation device
8 alternan-oligosaccharide, in the example: maltose alternan oligosaccharide (MAOS)
9 sucrose
10 feed
11 reactor
12 acceptor molecules, in the example: maltose
13 alternansucrase (AlSu)
14 alternan polymer (alternan polysaccharide)
15 leucrose
16 device comprising a membrane, in the example: membrane cell
17 membrane filtration; in the example: bioconversion and nanofiltration (constant volume diafiltration)

The invention claimed is:

1. A process for producing alternan-oligosaccharide, comprising contacting in a stirred tank reactor sucrose with a catalytically effective amount of alternansucrase enzyme and acceptor molecules with stirring, wherein the alternansucrase enzyme and acceptor molecules are present in the reactor in an aqueous liquid, wherein the alternansucrase enzyme is dissolved, emulsified, or suspended in the aqueous liquid, and the sucrose is continuously or half-continuously fed to the reactor, and wherein the sucrose and the acceptor molecules are converted to alternan-oligosaccharide, and fructose is formed as a by-product, continuously or half-continuously removing at least a part of the fructose and at least a part of leucrose, formed as a by product, from the reactor by membrane filtration, wherein removing of at least a part of the fructose and at least a part of leucrose comprises continuously or half-continuously circulating the content of the reactor through a device comprising a membrane and contacting the content of the reactor with the membrane, wherein at least a portion of the fructose at least a part of the leucrose and a portion of the aqueous liquid pass the membrane, and wherein a remainder, comprising the alternan-oligosaccharide, is returned to the reactor, wherein the average degree of polymerization DPw of the alternan-oligosaccharide is greater than 14.

2. The process of claim 1, wherein the membrane filtration is a diafiltration.

3. The process of claim 2, wherein further alternansucrase enzyme is fed to the reactor.

4. The process of claim 1, further comprising continuously or half-continuously feeding further aqueous liquid to the reactor.

5. The process of claim 4, wherein further alternansucrase enzyme is fed to the reactor.

6. The process of claim 1, further comprising continuously or half-continuously feeding further aqueous liquid to a reactor system comprising the reactor and the device comprising a membrane.

7. The process of claim 6, wherein further alternansucrase enzyme is fed to the reactor.

8. The process of claim 1, further comprising removing at least a part of an alternan-polysaccharide, which is formed as a further by-product, and at least a part of the alternan-sucrase enzyme.

9. The process of claim 8, further comprising removing at least a part of an alternan-polysaccharide by a further membrane filtration, wherein in the further membrane filtration the alternan-oligosaccharide is comprised in a permeate.

10. The process of claim 1, further comprising concentrating the alternan-oligosaccharide.

11. The process of claim 1, wherein an average degree of polymerization DPw or DPn of the alternan-oligosaccharide is regulated by the amount of the sucrose which is fed to the reactor.

12. The process of claim 1, wherein the feeding of the sucrose is stopped when a desired average degree of polymerization DPw or DPn of the alternan-oligosaccharide is reached.

13. The process of claim 1, wherein the weight average degree of polymerization DPw of the alternan-oligosaccharide is in a range of 5-30, as determined with GPC-RI.

14. The process of claim 1, wherein the weight average degree of polymerization DPw of the alternan-oligosaccharide is in a range of 10-20, as determined with GPC-RI.

15. The process of claim 1, wherein the acceptor molecules are maltose molecules.

16. The process of claim 1, wherein the sucrose is continuously fed and a rate of feed of sucrose, in molar amount of sucrose per time, is equal or substantially equal to a rate of continuous removal of fructose, in a molar amount of fructose per time, or wherein the ratio of the rate of feed of sucrose to the rate of removal of fructose is in the range of 1.2:1 to 1:1.

17. The process of claim 1, wherein a molar ratio of sucrose:acceptor molecules, which is the total amount of fed sucrose in relation to the total amount of acceptor molecules used in the process, is 10:1-30:1.

18. The process of claim 1, wherein further alternansucrase enzyme is fed to the reactor, preferably continuously or half continuously.

19. The process of claim 1, wherein a ratio of alternansucrase enzyme:sucrose, which is the total amount of fed sucrose, is 1000-10000 units (enzyme activity):1000 g of sucrose.

* * * * *